US010393668B2

(12) United States Patent
Takamoto et al.

(10) Patent No.: US 10,393,668 B2
(45) Date of Patent: Aug. 27, 2019

(54) PRODUCT INSPECTION DEVICE

(71) Applicant: SUM TECH INNOVATIONS CO., LTD., Okayama (JP)

(72) Inventors: Tomohisa Takamoto, Okayama (JP); Kazuhiko Inao, Okayama (JP); Takeshi Tsuji, Saitama (JP); Masanori Yoshimura, Okayama (JP)

(73) Assignee: SUM TECH INNOVATIONS CO., LTD, Okayama (JP)

( * ) Notice: Subject to any disclaimer, the term of this patent is extended or adjusted under 35 U.S.C. 154(b) by 0 days.

(21) Appl. No.: 15/527,925

(22) PCT Filed: Nov. 18, 2015

(86) PCT No.: PCT/JP2015/082464
§ 371 (c)(1),
(2) Date: May 18, 2017

(87) PCT Pub. No.: WO2016/080467
PCT Pub. Date: May 26, 2016

(65) Prior Publication Data
US 2018/0313767 A1 Nov. 1, 2018

(30) Foreign Application Priority Data
Nov. 19, 2014 (JP) .................. 2014-235113

(51) Int. Cl.
*G01N 21/85* (2006.01)
*G01N 21/88* (2006.01)
*G01N 21/84* (2006.01)

(52) U.S. Cl.
CPC ............. *G01N 21/85* (2013.01); *G01N 21/84* (2013.01); *G01N 21/88* (2013.01); *G01N 21/8806* (2013.01); *G01N 2201/0627* (2013.01)

(58) Field of Classification Search
CPC ........ G01N 21/84; G01N 21/85; G01N 21/88; G01V 5/0016; G01V 5/0025;
(Continued)

(56) References Cited

U.S. PATENT DOCUMENTS 5,335,791 A * 8/1994 Eason ................... B07C 5/3416
209/588
5,443,164 A * 8/1995 Walsh ................... B07C 5/3416
198/836.1
(Continued)

FOREIGN PATENT DOCUMENTS

JP 2006-3134 A 1/2006
JP 2007-305742 A 11/2007
(Continued)

OTHER PUBLICATIONS

Japan Patent Office, Written Opinion of the International Search Authority for PCT Application No. PCT/JP2015/082464. dated Feb. 16, 2016.
(Continued)

*Primary Examiner* — Sang H Nguyen
(74) *Attorney, Agent, or Firm* — SoCal IP Law Group LLP; Nikki M. Dossman

(57) ABSTRACT

Provided is an article inspection apparatus which does not arrange the LED mounting body by mistake at the time of mounting or replacing or the like and does not cause unevenness of irradiation light. The article inspection apparatus 1 includes a conveying device 2 that places an article on a translucent conveyor belt 16 and moves the article, a support base 3 that supports the conveying device 2, an irradiation device 4 that irradiates the conveyor belt 16 from below by disposing the LED mounting body 53 on which a semiconductor light emitting element is mounted and fixed on a printed circuit board 57, and a control device 5 that operates and controls the conveyor belt 16 and controls light
(Continued)

emission of the semiconductor light emitting element. In the LED mounting body 53, the white chip 58 and the RGB chip 59 are arranged in parallel on the printed circuit board 57 at predetermined intervals, and the wiring coupler 60 is disposed between the opposing white chip 58 and the RGB chip 59.

4 Claims, 9 Drawing Sheets

(58) Field of Classification Search
CPC .............. H05B 33/086; H05B 33/0869; H01L 2924/0002; H01L 2924/00; H01L 25/0753
See application file for complete search history.

(56) References Cited

U.S. PATENT DOCUMENTS

| | | | | |
|---|---|---|---|---|
| 5,526,119 A | * | 6/1996 | Blit | B07C 5/3422 |
| | | | | 209/577 |
| 5,600,303 A | * | 2/1997 | Husseiny | F41H 11/12 |
| | | | | 340/568.1 |
| 2010/0034353 A1 | * | 2/2010 | Kravis | G01V 5/0016 |
| | | | | 378/87 |
| 2011/0267825 A1 | * | 11/2011 | Hotta | C25D 11/04 |
| | | | | 362/296.02 |
| 2012/0008318 A1 | * | 1/2012 | Ishiwata | H05B 33/086 |
| | | | | 362/231 |
| 2014/0302253 A1 | * | 10/2014 | Lin | C01G 9/08 |
| | | | | 427/525 |
| 2015/0257224 A1 | * | 9/2015 | Timm | B64D 11/00 |
| | | | | 315/77 |

FOREIGN PATENT DOCUMENTS

| | | | |
|---|---|---|---|
| JP | 2008-227423 A | | 9/2008 |
| JP | 2009-44055 A | | 2/2009 |
| JP | 2013-3129 A | | 1/2013 |
| JP | 2013003129 A | * | 1/2013 |
| JP | 2013-93104 A | | 5/2013 |
| JP | 2014-22117 A | | 2/2014 |
| JP | 5763240 B1 | | 8/2015 |
| WO | 2016/080467 A1 | | 5/2016 |

OTHER PUBLICATIONS

Japan Patent Office, International Search Report for PCT Application No. PCT/JP2015/082464. dated Feb. 16, 2016.

* cited by examiner

[FIG.1]
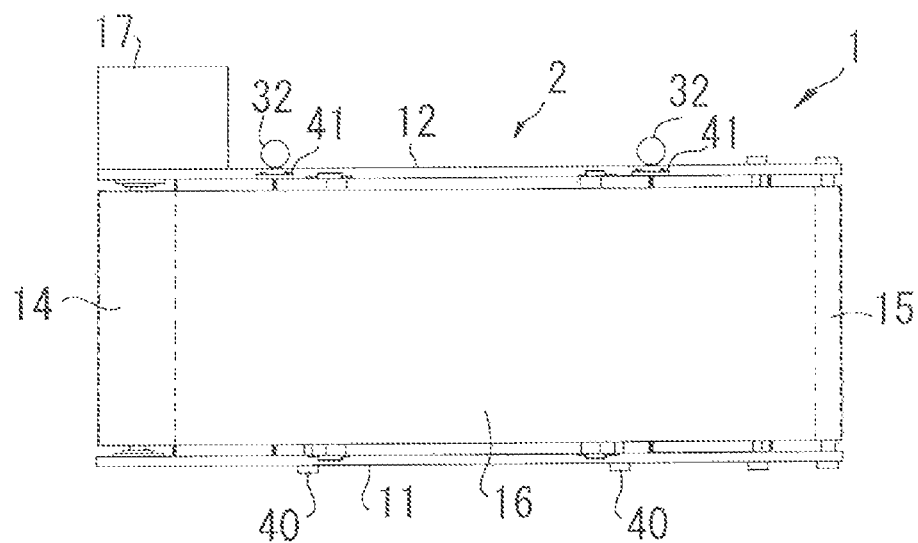
[FIG.2]
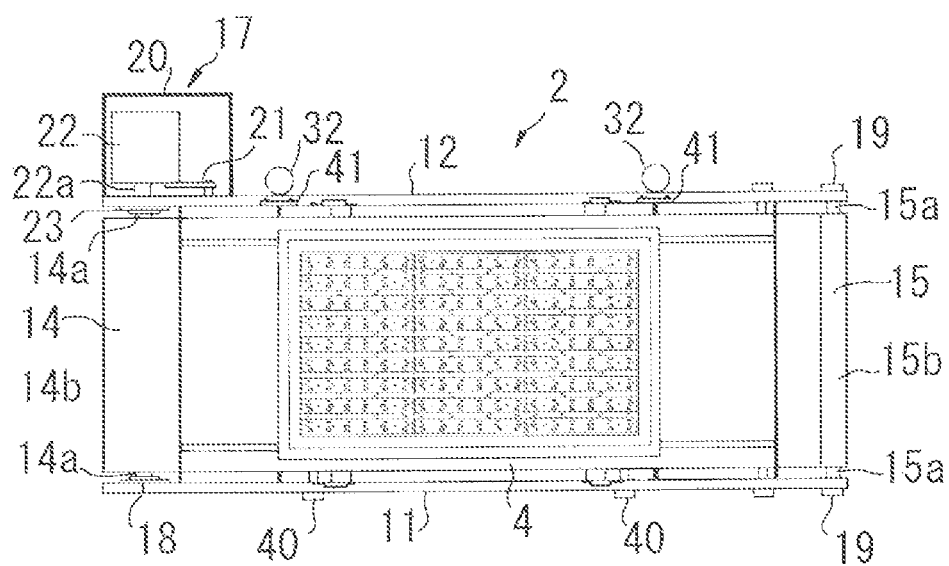

[FIG.3]
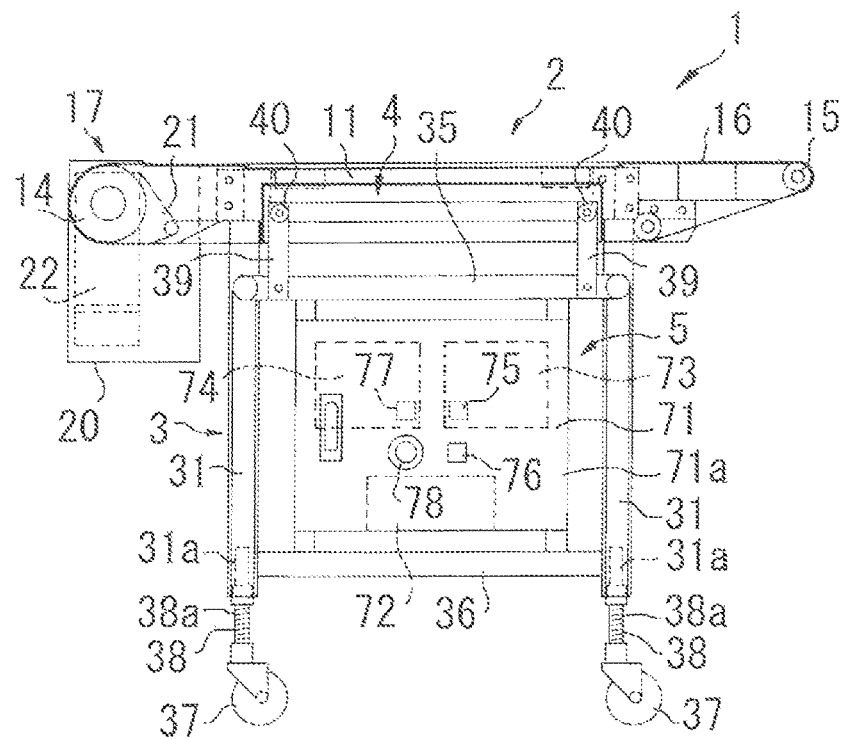
[FIG.4]
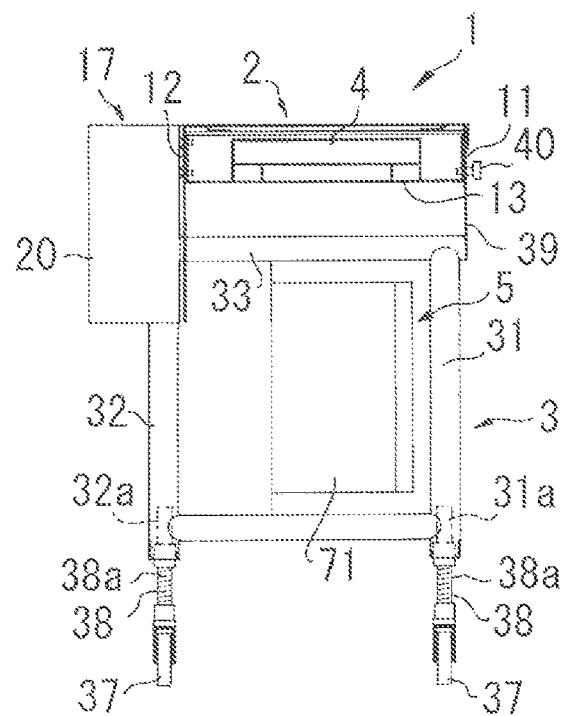

[FIG.5]
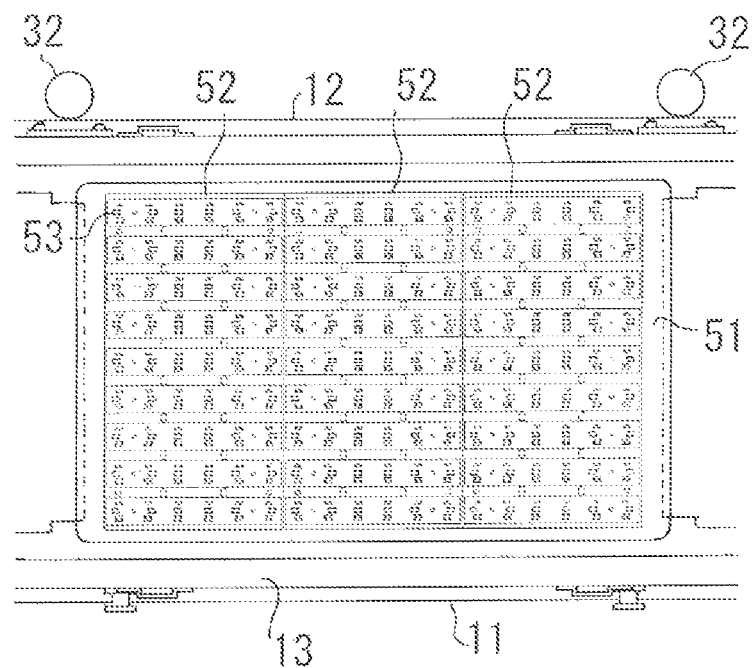
[FIG.6]
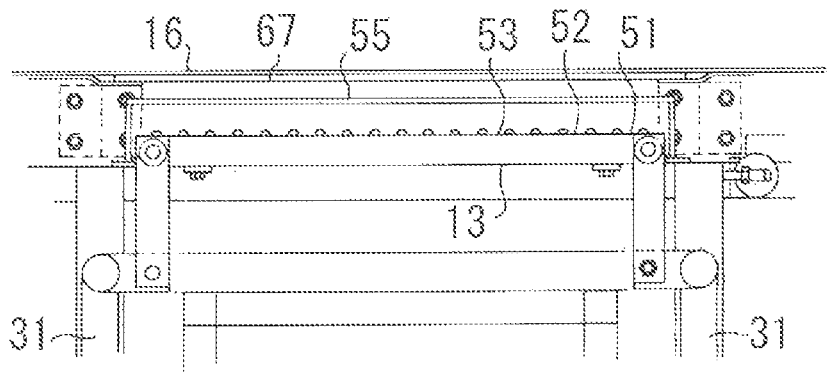

[FIG.7]
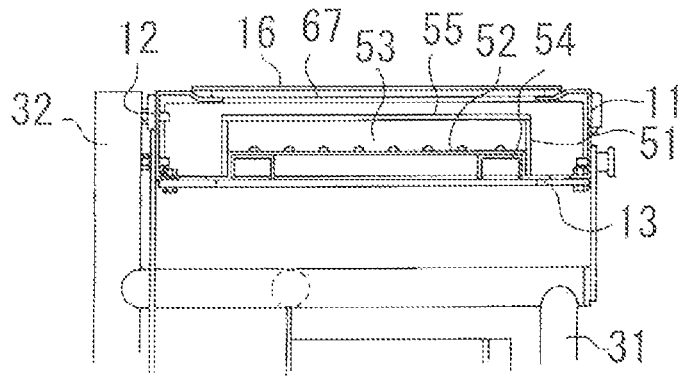
[FIG.8]
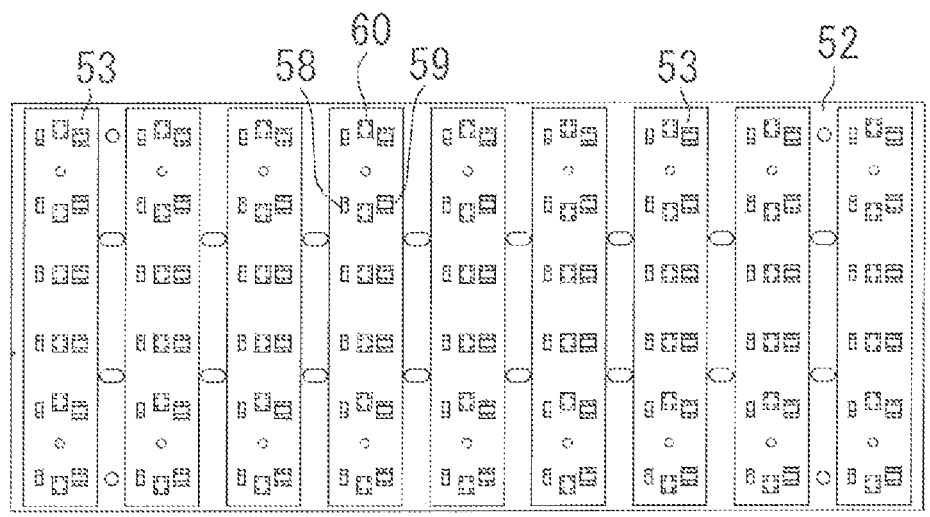

[FIG. 9]
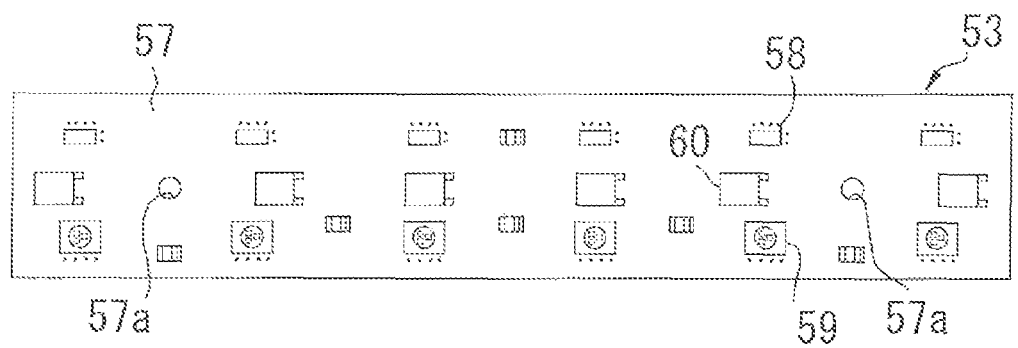
[FIG. 10]
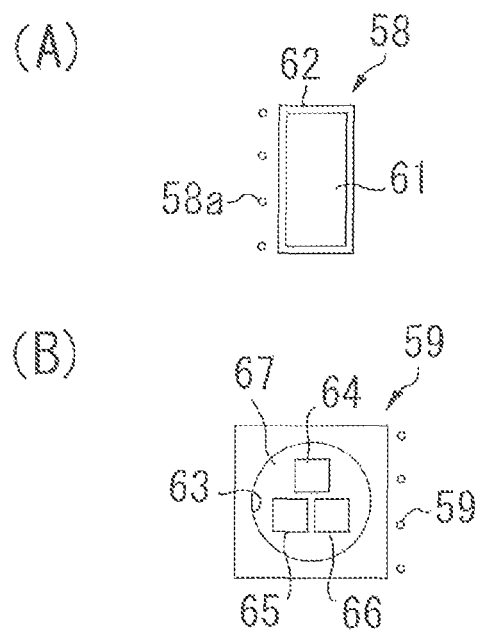

[FIG.11]
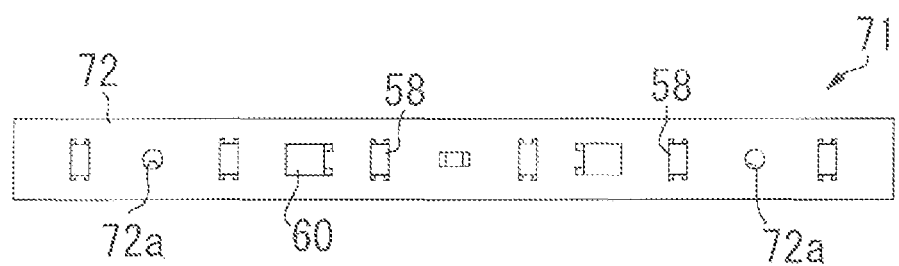

[FIG.12]
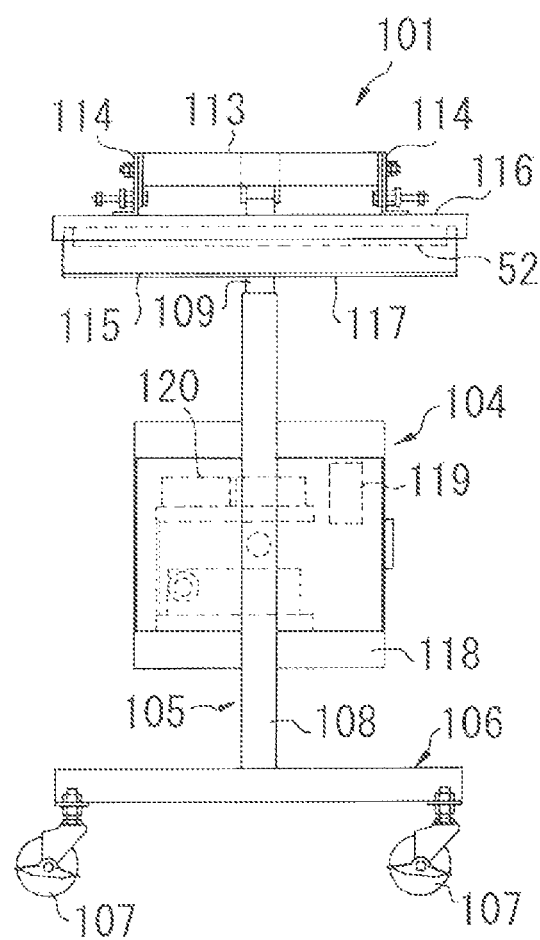

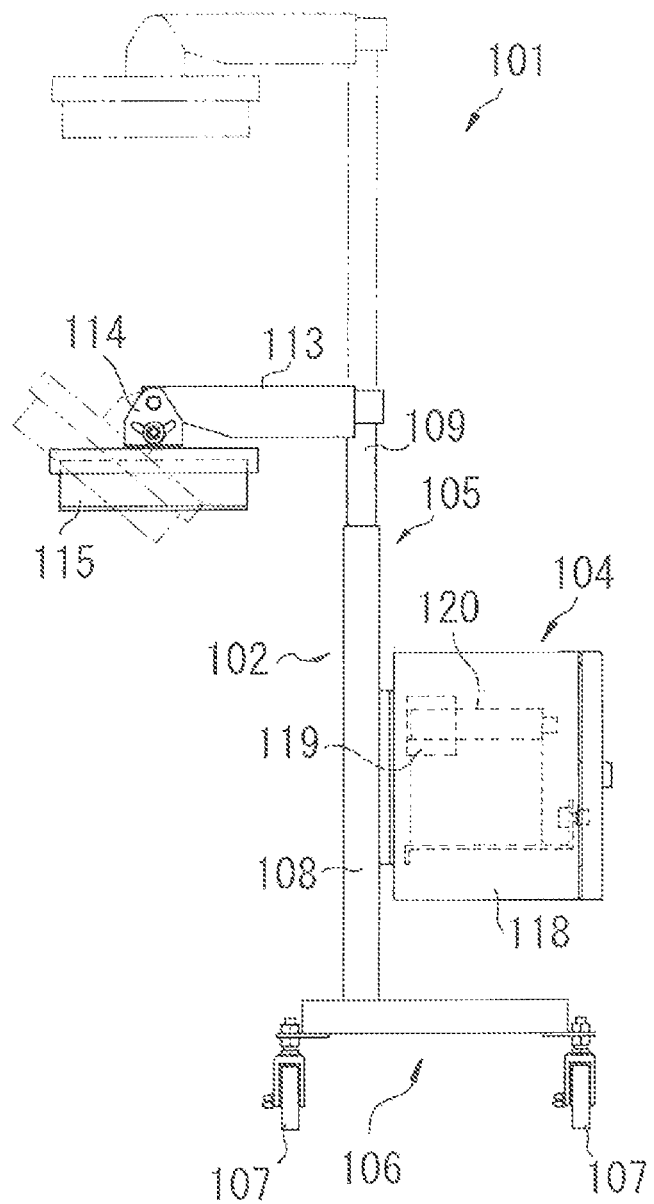
[FIG.13]

[FIG.14]
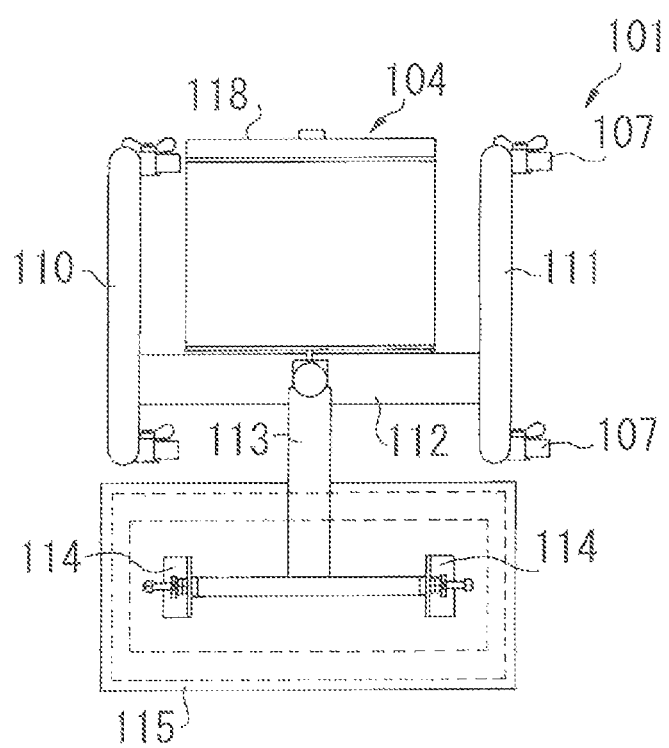

PRODUCT INSPECTION DEVICE

TECHNICAL FIELD

The present invention relates to an article inspection apparatus that conveys articles such as vegetables, fruits and other food items, beverages, medicines, packaging containers, electronic parts and the like, while inspecting whether a foreign object such as hair, dirt, small insect or the like is mixed in the article, or whether there is no defective part such as damage or breakage on the surface of the article and is used for sorting articles.

BACKGROUND ART

Conventionally, as an apparatus that conveys articles by a conveying device such as a belt conveyor while inspecting whether the foreign object such as hair, dirt, small insect or the like is mixed in the article, or whether there is no defective part such as damage or breakage on the surface of the article, an apparatus using visible light, X-ray or magnetic field is known.

However, an inspection apparatus using X-ray or magnetic field also has an influence on the human body of an inspection worker, care is also taken in handling, and in many cases, the inspection apparatus performs automatic inspection by an imaging device such as a camera, which is very expensive.

Therefore, for food items such as vegetables and fruits, visible light is applied in a process of placing and conveying a food item on a conveying device such as a belt conveyor, and a worker has seen through the interior of the food item and has inspected whether a foreign object such as hair, dirt, small insect or the like is mixed in the food item.

In order to further improve the efficiency of such inspection work, an inspection apparatus is known in which a translucent thin-walled conveyor belt having light permeability is used, and white light is applied from the lower side of the conveyor belt with a fluorescent lamp so that the worker can see through the interior of a food item (see Patent Literature 1).

However, in the inspection apparatus described in Patent Literature 1, a fluorescent lamp is used. Therefore, light flickers, an inspection worker tends to be fatigued, work efficiency declines in a short time, and in the long term there is a possibility of impairing visual acuity, which also poses a health problem.

Also, since white light is used, depending on the color of the food item such as blue, red and yellow, it has been difficult to see through the interior of the food item by the light transmitted through the food item and the light transmitted through the conveyor belt.

Furthermore, because fluorescent light is used, the electric power consumption is inevitably large, so that the electricity fee is inevitably expensive. The irradiation device is large, so that the whole apparatus has to be large in size as well.

Therefore, the inventors of the present application developed an article inspection apparatus that can solve the above problem, makes a worker less tired to maintain work efficiency, is free from the risk of impairing visual acuity, has no problem in terms of health, can efficiently perform visual inspection, has low power consumption, and can make the entire apparatus small (see Patent Literature 2).

CITATION LIST

Patent Literature

Patent Literature 1: Design Registration No. 1135732
Patent Literature 2: JP 2013-3129 A

SUMMARY OF THE INVENTION

Technical Problem

According to the article inspection apparatus described in Patent Literature 2, the above problem can be solved. However, since the LED mounting body emitting white light and the LED mounting body emitting red, green or blue light have substantially the same form, there is a concern that they are erroneously disposed at the time of mounting or replacing the LED mounting body or the like.

Further, the LED mounting body emitting white light and the LED mounting body emitting light of red, green or blue are respectively provided on separate printed circuit boards. Therefore, the positions and pitches of the white chip and the RGB chip on the printed circuit board are slightly shifted and unevenness occurs in the light applied onto the conveyor belt. Accordingly, a problem that the inspection worker is liable to be fatigued and work efficiency declines in a short time has occurred.

Furthermore, although it is necessary to supply a voltage to each LED mounting body, in the configuration like the above-described LED mounting body, it is troublesome to connect each LED mounting body with wiring, and it takes time to perform connection work.

The present invention has been made in view of the above problems, and an object thereof is to provide an article inspection apparatus that has no possibility of mistakenly arranging the LED mounting body emitting white light and the LED mounting body emitting red, green or blue light at the time of mounting or replacing the LED mounting body, has no problem that unevenness occurs in the light applied on the conveyor belt, the inspection worker is liable to be fatigued, and the work efficiency declines in a short time, can easily connect the LED mounting bodies with wires, and does not require long time for connection work.

Solution to the Problem

In order to achieve the above object, the article inspection apparatus of the present invention includes a conveying device that places an article on a translucent conveyor belt and moving the article, a support base that supports the conveying device, an irradiation device that irradiates the conveyor belt from below by disposing the LED mounting body on which a semiconductor light emitting element is mounted and fixed on a printed circuit board, and a control device that operates and controls the conveyor belt and controls light emission of the semiconductor light emitting element, and the LED mounting body is characterized in that a white chip and an RGB chip are arranged in parallel on a printed circuit board at predetermined intervals and a wiring coupler is disposed between the opposing white chip and the RGB chip.

Here, it is preferable to drill a plurality of micropores near the white chip and the RGB chip of the printed circuit board.

The RGB chip is characterized in that a semiconductor light emitting element (LED) that emits red (R), a semiconductor light emitting element (LED) that emits green (G), and a semiconductor light emitting element (LED) that emits blue (B) are arranged in a window frame, and a coating layer is formed on the semiconductor light emitting elements (LED) with a material such as silicon, epoxy or the like.

It is preferable that the control device enables each of the plurality of semiconductor light emitting elements to emit light individually and can set the light emission amount of the semiconductor light emitting element separately.

Advantageous Effects of Invention

In the article inspection apparatus of the present invention, since the LED mounting body is configured such that the white chip and the RGB chip are arranged in parallel at predetermined intervals on the printed circuit board, there is no possibility of mistakenly arranging the LED mounting body emitting white light and the LED mounting body emitting red, green or blue light at the time of mounting or replacing the LED mounting body, and a problem that unevenness occurs in the light applied onto the conveyor belt, the inspection worker is liable to be fatigued, and the work efficiency declines in a short time does not occur.

Furthermore, since the wiring coupler is disposed between the opposing white chip and the RGB chip, wiring couplers of adjacent LED mounting bodies can be connected by wiring, and it is easy to connect each LED mounting body with wiring, and time is not required for connection work.

BRIEF DESCRIPTION OF DRAWINGS

FIG. 1 is a plan view of an article inspection apparatus of the present invention.
FIG. 2 is a plan view of a state in which a conveyor belt is removed in the article inspection apparatus of the present invention.
FIG. 3 is a front view of the article inspection apparatus of the present invention.
FIG. 4 is a side view of the article inspection apparatus of the present invention.
FIG. 5 is an enlarged plan view of an installation portion of an irradiation device in FIG. 2.
FIG. 6 is an enlarged front view of an installation portion of an irradiation device in FIG. 3.
FIG. 7 is an enlarged side view of an installation portion of an irradiation device in FIG. 4.
FIG. 8 is a plan view showing a state in which an LED mounting body is fixed and arranged on a support plate.
FIG. 9 is a plan view of the LED mounting body.
FIG. 10A is a plan view enlarging the vicinity of a white chip and FIG. 10B is a plan view enlarging the vicinity of a RGB chip, in FIG. 9.
FIG. 11 is a plan view of the LED mounting body.
FIG. 12 is a front view of the article inspection apparatus of the present invention.
FIG. 13 is a side view of the article inspection apparatus of the present invention.
FIG. 14 is a plan view of the article inspection apparatus of the present invention.

DESCRIPTION OF EMBODIMENTS

Hereinafter, preferred embodiments of the article inspection apparatus of the present invention will be described in detail with reference to the drawings.

FIG. 1 is a plan view of an article inspection apparatus of the present invention, FIG. 2 is a plan view of a state in which a conveyor belt is removed in the article inspection apparatus of the present invention, FIG. 3 is a front view of the article inspection apparatus of the present invention, and FIG. 4 is a side view of the article inspection apparatus of the present invention.

The article inspection apparatus 1 of the present invention includes a conveying device 2, a support base 3, an irradiation device 4, and a control device 5.

The conveying device 2 includes side frames 11, 12, a bottom frame 13, a driving roller 14, a driven roller 15, a conveyor belt 16, and a driving device 17.

Both end portions of the bottom frame 13 are fixed to the lower end portions of the side frames 11, 12, and the driving roller 14 and the driven roller 15 are disposed at both end portions of the side frames 11, 12.

One end portion of a shaft portion 14a of the driving roller 14 is rotatably supported by the side frame 11 via a bearing 18 and the other end portion is rotatably supported by the side frame 12 via the bearing 18.

One end portion of a shaft portion 15a of the driven roller 15 is rotatably supported by the side frame 11 via a bearing 19 and the other end portion is rotatably supported by the side frame 12 via the bearing 19.

The driving device 17 supports a drive motor 22 via a bracket 21 in a housing 20, and a drive shaft 22a of the drive motor 22 and the shaft portion 14a of the driving roller 14 are connected via a joint 23.

The conveyor belt 16 is stretched across a trunk portion 14b of the driving roller 14 and a trunk portion 15b of the driven roller 15. By driving the drive motor 20 and rotating the driving roller 14, the conveyor belt 16 is operated and moved.

Here, the conveyor belt 16 for use is obtained by molding a transparent or translucent white synthetic rubber such as urethane rubber or ethylene-propylene rubber (EPM).

The support base 3 includes front support columns 31, 31, rear support columns 32, 32, connecting members 33, 33, connecting members 34, 34, a connecting member 35, a connecting member 36, and casters 37, 37, 37, 37.

The connecting members 33, 33 connect the upper end portions of the front support columns 31, 31 and the rear support columns 32, 32, and the connecting members 34, 34 connect the lower end portions of the front support columns 31, 31 and the rear support columns 32, 32, the connecting member 35 connects the connecting members 33, 33 to each other, and the connecting member 36 connects the connecting members 34, 34 to each other.

Female screw portions 31a, 31a, 32a, 32a formed at the lower end portions of the front support columns 31, 31 and the rear support columns 32, 32 and male screw portions 38a, 38a, 38a, 38a formed on the support shafts 38, 38, 38, 38 are screwed together. Accordingly, casters 37, 37, 37, 37 are attached to the front support columns 31, 31 and the rear support columns 32, 32 via support shafts 38, 38, 38, 38.

Therefore, by appropriately rotating the support shafts 38, 38, 38, 38, the heights of the front support columns 31, 31 and the rear support columns 32, 32 can be adjusted.

By fastening the lower end portions of the supporting members 39 and 39 to the front end portions of the connecting members 33, 33, by fixing the upper end portion thereof to an intermediate portion of the side frame 11 via the support shafts 40, 40, and by fixing the intermediate portion of the side frame 12 to the upper end portions of the rear support columns 32, 32 via the support members 41, 41, the conveying device 2 is placed on the support base 3.

The irradiation device 4 includes a supporting member 51, support plates 52, 52, 52, a plurality of LED mounting bodies 53, and a cover member 55.

The support plates 52, 52, 52 are fixed to the upper surface of the supporting member 51 by screws 56, 56, . . . . As shown in FIG. 8, the plurality of LED mounting bodies 53 are fixed to the upper surface of each supporting plate 52 by the screws 56, 56, . . . at predetermined intervals.

As shown in FIG. 9, the LED mounting body 53 has a white chip 58 and an RGB chip 59 arranged on a printed circuit board 57 at predetermined intervals. A wiring coupler 60 is disposed between the opposing white chip 58 and the RGB chip 59. In addition, insertion holes 57a, 57a are formed in the printed circuit board 57 near both end portions.

As shown in FIG. 10(A), the white chip 58 is formed by forming the coating layer 62 in which a material such as silicon, epoxy or the like is applied to yellow on a semiconductor light emitting element (LED) 61 that emits blue (B) light. As a result, white light is emitted.

Further, near the white chip 58 of the printed circuit board 57, a plurality of micropores 58a, 58a . . . for radiating heat are formed. The diameter of the micropore 58a is preferably 0.1 to 0.5 mm and the pitch is preferably 1.0 to 1.5 mm.

As shown in FIG. 10(B), the RGB chip 59 includes a semiconductor light emitting element (LED) 64 that emits red (R) light, a semiconductor light emitting element (LED) 65 that emits green (G) light, and a semiconductor light emitting element (LED) 66 that emits blue (B) light, in a window frame 63. The coating layer 67 is formed on the semiconductor light emitting elements (LED) 64, 65, and 66 with a material such as silicon, epoxy or the like. As a result, red, green or blue light is individually emitted.

Further, near the RGB chip 59 of the printed circuit board 57, a plurality of micropores 59a, 59a . . . for radiating heat are formed. The diameter of the micropore 59a is preferably 0.1 to 0.5 mm and the pitch is preferably 1.0 to 1.5 mm.

As described above, in the article inspection apparatus 1 of the present invention, since the LED mounting body 53 is configured such that the white chip 58 and the RGB chip 59 are arranged in parallel at predetermined intervals on the printed circuit board 57, there is no possibility of mistakenly arranging the LED mounting body emitting white light and the LED mounting body emitting red, green, or blue light at the time of mounting or replacing the LED mounting body 53, and a problem that unevenness occurs in the light applied on the conveyor belt 16, the inspection worker is liable to be fatigued, and the work efficiency declines in a short time does not occur.

Furthermore, since the wiring coupler 60 is disposed between the opposing white chip 58 and the RGB chip 59, wiring couplers 60, 60 of adjacent LED mounting bodys 53, 53 can be connected by wiring, and it is easy to connect each LED mounting body 53 with wiring, and long time is not required for connection work.

The LED mounting body 53 can be fixed to the support plate 52 by inserting the screws 56, 56 into the insertion holes 57a, 57a of the printed circuit board 57.

The cover member 55 is molded with a colorless and transparent synthetic resin such as polycarbonate, acrylic or the like, and is disposed so as to cover the LED mounting body 53.

Further, as shown in FIG. 7, a protective plate member 68 is disposed over the upper end portion of the side frame 11 of the conveying device 2 and the upper end portion of the side frame 12. The protective plate member 68 is also formed of a colorless and transparent synthetic resin such as polycarbonate, acrylic or the like.

The control device 5 is provided with a power supply 72, a drive control circuit board 73, a light emission control circuit board 74 and the like in a housing 71. A motor drive button 75, a motor stop button 76, an LED light emission button 77, and an emergency stop button 78 are disposed on the front panel 71a of the housing 71.

A rotation speed adjustment dial is provided on the drive control circuit board 73, and by appropriately operating the rotation speed adjustment dial, the rotation speed of the drive motor 22 can be set.

On the light emission control circuit board 74, the light emission amount adjustment dials of the semiconductor light emitting elements (LEDs) 61, 64, 65, 66 are disposed. By suitably operating the light emission amount adjustment dial, the semiconductor light emitting elements (LEDs) 61, 64, 65, 66 can be made to emit light and the light emission amount can be set.

After setting the rotation speed of the drive motor 22 in advance and setting the light emission amounts of the semiconductor light emitting elements (LEDs) 61, 64, 65, 66, when the motor drive button 75 is pressed, the drive motor 22 is driven and the conveyor belt 16 starts moving. When the motor stop button 76 is pressed, the drive motor 22 stops and the conveyor belt 16 stops.

Further, when the LED light emission button 77 is pressed, the semiconductor light emitting elements (LEDs) 61, 64, 65, 66 that are enabled to emit light start emitting light with the set light emission amount.

Here, as the illuminance on the surface of the conveyor belt 16, it is preferable that the illuminance of the semiconductor light emitting element 61 (white) is set to 50 to 70 lm (lumen)/cm$^2$, the illuminance of the semiconductor light emitting element 64 (red) is set to 25 to 45 lm/cm$^2$, the illuminance of the semiconductor light emitting element 65 (green) is set to 50 to 70 lm/cm$^2$, and the illuminance of the semiconductor light emitting element 66 (blue) is set to 5 to 25 lm/cm$^2$. The numerical values of the semiconductor light emitting elements 64, 65, 66 take into account the case where each color is additive mixed.

In the case where an emergency occurs, such as when the conveyor belt 16 performs an abnormal operation or in the case where the semiconductor light emitting elements (LEDs) 61, 64, 65, 66 abnormally emit light, when the emergency stop button 78 is pressed, the power supply 72 of the light transmitting article inspection apparatus 1 is cut off and immediately stopped.

Since the light transmitting article inspection apparatus 1 of the present invention has the above-described configuration, an apparatus administrator previously sets the rotational speed of the drive motor 22, and sets whether or not the semiconductor light emitting elements (LEDs) 61, 64, 65, 66 can emit light, and sets the light emission amount, in correspondence with the article to be inspected.

At the time of inspecting the article, an inspection worker can first cause the semiconductor light emitting elements (LED) 61, 64, 65, 66 to emit light with a predetermined light emission amount by pressing the LED light emission button 77.

At this time, if only the semiconductor light emitting element (LED) 61 is set to emit light, a voltage is applied only to the semiconductor light emitting element (LED) 61 of the LED mounting body 53. Thus, only the white light is emitted, passes through the cover member 55 and the protective plate member 68, and is applied on the translucent conveyor belt 16.

Also, if only one of the semiconductor light emitting elements (LEDs) 64, 65, 66 is set to emit light, a voltage is applied to only one of the semiconductor light emitting elements (LEDs) 64, 65, 66 of the RGB chip 59. Thus, only one of red, green, and blue light is emitted, passes through the cover member 55 and the protective plate member 68, and is applied on the translucent conveyor belt 16.

Also, if any one of the semiconductor light emitting elements (LED) 64, 65, 66 is set to emit light at the same time, a voltage is simultaneously applied to any one of the semiconductor light emitting elements (LED) 64, 65, 66 of the RGB chip 59. Red, green or blue light is emitted at the same time and becomes light of a predetermined color by additive color mixing, passes through the cover member 55 and the protective plate member 68, and is applied on the translucent conveyor belt 16.

Next, by pressing the motor drive button 75, the inspection worker can drive the drive motor 22 and move the conveyor belt 16 at a predetermined speed.

Then, when food items such as vegetables and fruits are placed on the conveyor belt 16, the food items can be conveyed by the conveyor belt 16.

When the food item reaches the irradiation areas of the semiconductor light emitting elements (LEDs) 61, 64, 65, 66, the inspection worker visually observes the food item irradiated with white light or predetermined color light, and inspects whether a foreign object such as hair, dirt, small insect or the like is mixed in the food items.

When a foreign object such as hair, dust, small insects, etc. are mixed, the inspection operator removes the food item from the conveyor belt 16 or moves the food item to a side end portion of the conveyor belt 16, and sorts the excellent item and the defective item.

In general, an article is inspected by applying white light in many cases. However, when inspecting an article in which white tofu is wrapped with a transparent synthetic resin film, it is possible to more easily confirm the foreign object mixed in the synthetic resin film, damaged or broken portion in the synthetic resin film by applying red, green or blue light rather than white light.

Also, in a vegetable or fruit having colors such as green, red or the like on the outer leave or the outer skin, it is easier to confirm a foreign object mixed in the inner leave of the vegetable or the pulp of the fruit by applying light of a color different from the color of the outer leave or the outer skin.

The article inspection apparatus 1 of the present invention uses the semiconductor light emitting elements (LED) 61, 64, 65, 66, and since the light is stably applied without causing the light to flicker, it is difficult for the inspection worker to be fatigued, and it is possible to maintain the efficiency of the inspection work for a long time. There is no fear of impairing visual acuity, and there is no health problem.

In addition, it is possible to emit light by selecting not only white light, but also red light, green light or blue light, and furthermore, by selecting appropriate color light obtained by additive color mixture of these color lights. Therefore, it is possible to apply light of an appropriate color corresponding to the color of the article such as blue, red, yellow, etc., so that the interior of the article can be more easily viewed and the inspection can be made efficient.

Furthermore, since the semiconductor light emitting elements (LEDs) 61, 64, 65, 66 are used, the power consumption is also reduced, the electricity fee can be reduced, the irradiation device can be smaller, and the entire device can also be downsized.

In the above embodiment, the LED mounting body 53 has the white chip 58 and the RGB chip 59 arranged at predetermined intervals on the printed circuit board 57. However, as shown in FIG. 11, the LED mount body 71 in which the white chip 58 and the wiring coupler 60 are arranged at predetermined intervals on the printed circuit board 72 may be used. Similarly, insertion holes 72a, 72a are formed in the printed circuit board 72 near both end portions.

In the above embodiment, only the LED mounting body 53 or the LED mounting body 71 is fixed to the support plate 52, but the LED mounting body 53 and the LED mounting body 71 may be alternately arranged and fixed on the support plate 52.

Incidentally, the article inspection apparatus 1 of the present invention is not limited to that described in the above embodiment, and may be a support base for fixing without adopting the casters 37, 37, . . . .

Further, as shown in FIGS. 12 to 14, an article inspection apparatus 101 in which the conveying device 2 or the support base 3 is formed as a separate body may be adopted.

This article inspection apparatus 101 includes a support mechanism 102, an irradiation device 103, and a control device 104.

The support mechanism 102 includes a support column 105, a leg body 106, and casters 107, 107, 107, 107.

The support column 105 includes a lower support column 108 and an upper support column 109, and the upper support column 109 is extensible.

In the leg body 106, a left leg body 110 and a right leg body 111 are connected by a connecting member 112, and the lower support column 108 is fastened onto the connecting member 112.

The casters 107, 107, 107, 107 are attached to both end portions of the left leg body 110 and the right leg body 111.

The irradiation device 103 includes an elevating member 113, supporting members 114, 114, and irradiation frame 115.

The elevating member 113 is a member exhibiting a T-shape when viewed from the plane, and a base end portion thereof is fastened to the upper end portion of the upper support column 109, and the supporting members 114, 114 are rotatably fixed to both ends of the front end portion.

The supporting members 114, 114 pivotally support the upper end portion on both sides of the front end portion of the elevating member 113, and the lower end portion is fastened to the upper surface of the irradiation frame 115.

The irradiation frame 115 includes a supporting member 116, the support plates 52, 52, 52, a plurality of LED mounting bodies 53, and the cover member 117.

The supporting member 116 is disposed inside the irradiation frame 115 and the support plates 52, 52, 52 are fixed to the lower surface of the supporting member 116 by screws 56, 56, . . . , and the cover member 117 is disposed at the lower surface of the irradiation frame 115.

Here, the support plates 52, 52, 52 and the LED mounting body 53 have the same structure as those of the above embodiment, and the cover member 117 is made of the same material as the cover member 55.

The control device 104 is provided with a power supply 119, a light emission control circuit board 120, and the like in a housing 118, and is fastened to the rear surface of the lower support column 108.

The article inspection apparatus 101 of the present invention has the above-described configuration. Therefore, by disposing a separate conveying device or support base in front of the support column 105, and applying light from the irradiation frame 115 positioned above to the conveying

REFERENCE SIGNS LIST

1 Article inspection apparatus
2 Conveying device
3 Support base
4 Irradiation device
5 Control device
16 Conveyor belt
53 LED mounting body
57 Printed circuit board
58 White chip
58a Micropore
59 RGB chip
59a Micropore
60 Wiring coupler
61 Semiconductor light emitting element
63 Window frame
64, 65, 66 Semiconductor light emitting element
67 Coating layer It is claimed:

1. An article inspection apparatus comprising:
a conveying device that places an article on a translucent conveyor belt and moves the article;
a support base that supports the conveying device;
an irradiation device that irradiates the conveyor belt from below by disposing the LED mounting body on which a semiconductor light emitting element is mounted and fixed on a printed circuit board; and
a control device that operates and controls the conveyor belt and controls light emission of the semiconductor light emitting element, wherein
in the LED mounting body, a plurality of white chips and a plurality of RGB chips are arranged in the longitudinal direction at predetermined intervals in parallel on the printed circuit board and a plurality of wiring couplers are also arranged in the longitudinal direction at predetermined intervals between the opposing white chips and the RGB chips on the printed circuit board.

2. The article inspection apparatus according to claim 1, wherein a plurality of micropores are formed nearly around the white chip and the RGB chip on the printed circuit board.

3. The article inspection apparatus according to claim 1, wherein the RGB chip includes a semiconductor light emitting element (LED) that emits red (R) light, a semiconductor light emitting element (LED) that emits green (G) light, and a semiconductor light emitting element (LED) that emits blue (B) light, in a window frame, and a coating layer is formed on the semiconductor light emitting elements (LED) with silicon or epoxy material.

4. The article inspection apparatus according to claim 1, wherein the control device enables each of the plurality of semiconductor light emitting elements to emit light individually and can set the light emission amount of the semiconductor light emitting element separately.

* * * * *